US011999388B2

(12) United States Patent
Liu et al.

(10) Patent No.: US 11,999,388 B2
(45) Date of Patent: Jun. 4, 2024

(54) INTERIOR AIR QUALITY MONITORING AND VENTILATION CONTROL METHOD AND SYSTEM FOR TRAIN

(71) Applicant: CENTRAL SOUTH UNIVERSITY, Hunan (CN)

(72) Inventors: Hui Liu, Hunan (CN); Yanfei Li, Hunan (CN); Rui Yang, Hunan (CN); Shuqin Dong, Hunan (CN); Chengqing Yu, Hunan (CN)

(73) Assignee: Central South University, Hunan (CN)

( * ) Notice: Subject to any disclaimer, the term of this patent is extended or adjusted under 35 U.S.C. 154(b) by 192 days.

(21) Appl. No.: 17/292,281

(22) PCT Filed: Jul. 29, 2020

(86) PCT No.: PCT/CN2020/105472
§ 371 (c)(1),
(2) Date: May 7, 2021

(87) PCT Pub. No.: WO2021/023075
PCT Pub. Date: Feb. 11, 2021

(65) Prior Publication Data
US 2022/0153320 A1 May 19, 2022

(30) Foreign Application Priority Data
Aug. 2, 2019 (CN) .......................... 201910714887.3

(51) Int. Cl.
B61D 27/00 (2006.01)
B60H 1/00 (2006.01)
G06N 3/08 (2023.01)

(52) U.S. Cl.
CPC ......... B61D 27/009 (2013.01); B60H 1/0073 (2019.05); B60H 1/008 (2013.01);
(Continued)

(58) Field of Classification Search
CPC ...... B61D 27/00; B61D 27/009; B60H 1/008; B60H 1/0073; B60H 1/00821; G06N 3/08; G01N 2015/0046
(Continued)

(56) References Cited

FOREIGN PATENT DOCUMENTS

CN 104374053 A 2/2015
CN 105972782 A 9/2016
(Continued)

OTHER PUBLICATIONS

English abstract of CN104374053A.
(Continued)

Primary Examiner — Allen R. B. Schult
(74) Attorney, Agent, or Firm — Caesar Rivise, PC

(57) ABSTRACT

The present invention discloses an interior air quality monitoring and ventilation control method and system for a train. The interior air quality monitoring and ventilation control method for the train comprises: acquiring multiple groups of interior and exterior air quality detection data; acquiring interior and exterior air comprehensive evaluation index $Q_0$ and $Q_1$ by using the experimental data; training an exterior fresh air volume control model if $Q_0 \geq Q_1$, or else training an interior air purification control model; detecting the interior and exterior air quality detection data; acquiring the interior and exterior air comprehensive evaluation index $Q_0$ and $Q_1$ by using the detection data; if $Q_0 \geq Q_1$, calling the exterior fresh air volume control model to obtain the required ventilation volume level and controlling a ventilation system with the output result; otherwise, calling the interior air purification control model to obtain the required ventilation volume level and air purification device power level, controlling the ventilation system and the air purification device with the output results. The present invention can apply suitable ventilation control strategies according to different
(Continued)

degrees of air quality, to achieve a health guarantee for the interior air quality of the high-speed train under the conditions of energy conservation and environmental protection.

15 Claims, 2 Drawing Sheets

(52) U.S. Cl.
CPC ......... *B60H 1/00821* (2013.01); *B61D 27/00* (2013.01); *G06N 3/08* (2013.01)

(58) Field of Classification Search
USPC .......................................................... 454/75
See application file for complete search history.

(56) References Cited

FOREIGN PATENT DOCUMENTS

| | | | |
|---|---|---|---|
| CN | 106196505 | A | 12/2016 |
| CN | 106777863 | A | 5/2017 |
| CN | 107477782 | A2 | 12/2017 |
| CN | 108510129 | A | 9/2018 |
| CN | 108572648 | A | 9/2018 |
| CN | 110069087 | A | 7/2019 |
| CN | 110395286 | A | 11/2019 |
| KR | 20150132680 | A | 11/2015 |
| KR | 20190043258 | A | 4/2019 |

OTHER PUBLICATIONS

English abstract of CN105972782A.
English abstract of CN106196505A.
English abstract of CN106777863A.
English abstract of CN107477782A.
English abstract of CN108510129A.
English abstract of CN110395286A.
English abstract of CN110069087A.
English abstract of KR20150132680A.
English abstract of KR20190043258A.
English abstract of CN108572648A.
International Search report for corresponding PCT Application No. PCT/CN2020/105472 dated Aug. 31, 2020.

INTERIOR AIR QUALITY MONITORING AND VENTILATION CONTROL METHOD AND SYSTEM FOR TRAIN

CROSS-REFERENCE TO RELATED APPLICATIONS

This application is a U.S. National Phase Application under 35 U.S.C. § 371 of PCT/CN2020/105472, filed Jul. 29, 2020, which claims priority from Chinese Patent Application No. 201910714887.3, filed Aug. 2, 2019, the contents of which applications are incorporated herein by reference in their entireties.

FIELD OF THE INVENTION

The present invention particularly relates to an interior air quality monitoring and ventilation control method and system for a train.

BACKGROUND OF THE INVENTION

With rapid development of China's high-speed trains and people's increasing material and culture levels, people now have increasingly high requirements for comfort in compartments besides safety and reliability requirements for high-speed trains.

The air quality in a compartment of a high-speed train directly affects the comfort of passengers. Therefore, monitoring and controlling the air quality in the train play an important role in the comfort of the train.

In addition, energy and environment are also subjects in modern times. Implementing different ventilation adjustment schemes for different air qualities in the trains is conducive to the development of energy-saving, comfortable and reliable high-speed trains.

SUMMARY OF THE INVENTION

An objective of the present invention is to provide an interior air quality monitoring and ventilation control method and system for a train in order to improve the comfort of passengers in the train, which can select suitable ventilation control strategies according to different degrees of air quality, so as to achieve a health guarantee for the interior air quality of the high-speed train under the conditions of energy conservation and environmental protection.

In order to solve the above technical problems, the technical solution adopted by the present invention is as follows:

An interior air quality monitoring and ventilation control method for a train includes the following steps:
step 1, acquiring multiple groups of interior air quality detection data and exterior air quality detection data;
step 2, acquiring an interior air comprehensive evaluation index $Q_0$ by using the interior air quality detection data in step 1, and acquiring an exterior air comprehensive evaluation index $Q_1$ by using the exterior air quality detection data in step 1;
step 3, determining the magnitude relationship between $Q_0$ and $Q_1$ obtained in step 2, and if $Q_0 \geq Q_1$, skipping to step 41; otherwise, skipping to step 51;
step 41, training an exterior fresh air volume control model according to the following method:
   selecting n1 groups of corresponding interior air quality detection data and corresponding exterior air quality detection data as experimental data;
   setting the ventilation volume level of a ventilation system of the high-speed train to a G1 level; performing ventilation experiments on the train under the conditions of n1 groups of experimental data, to obtain a minimum ventilation volume level that can reduce the interior air quality to a human health value within 5 minutes, as a ventilation volume level label corresponding to each group of experimental data; and
   training an exterior fresh air volume control model by taking the n1 groups of experimental data as input and taking the ventilation volume level labels corresponding to the n1 groups of experimental data as output to obtain the exterior fresh air volume control model;
step 51, training an interior air purification control model according to the following method:
   selecting n2 groups of corresponding interior air quality detection data and corresponding exterior air quality detection data as experimental data;
   setting the ventilation volume level of the ventilation system of the high-speed train to a G1 level, and setting the power level of an air purification device to a G2 level;
   performing ventilation experiments on the train under the conditions of n2 groups of experimental data, to obtain a minimum ventilation volume level and a minimum power level of the air purification device that can reduce the air quality to the human health value within 5 minutes, wherein the obtained minimum ventilation volume level is used as a ventilation volume level label corresponding to each group of experimental data, and the obtained minimum power level of the air purification device is used as a power level label of the air purification device corresponding to each group of experimental data; and
   training an interior air purification control model by taking the n2 groups of experimental data as input and taking the ventilation volume level labels and the power level labels of the air purification device corresponding to the n2 groups of experimental data as output to obtain the interior air purification control model;
step 6, detecting an interior air quality detection data and an exterior air quality detection data;
step 7, acquiring an interior air comprehensive evaluation index $Q_0$ by using the interior air quality detection data in step 6, and acquiring an exterior air comprehensive evaluation index $Q_1$ by using the exterior air quality detection data in step 6; and
step 8, determining the magnitude relationship between $Q_0$ and $Q_1$ obtained in step 7:
   if $Q_0 \geq Q_1$, calling the exterior fresh air volume control model to obtain the required ventilation volume level and controlling the ventilation system of the high-speed train with the ventilation volume level;
   otherwise, calling the interior air purification control model to obtain the required ventilation volume level and power level of the air purification device, controlling the ventilation system of the train with the ventilation volume level, and controlling the air purification device with the power level of the air purification device.

As a preferred mode, the interior air quality detection data and the exterior air quality detection data both include one or more of CO2 concentration, NO2 concentration, SO2 concentration, PM2.5 concentration, VOC concentration, and dust concentration.

As a preferred mode, the interior air quality detection data and/or the exterior air quality detection data are obtained by a multi-point monitoring mode.

As a preferred mode,
a calculation method of the interior air comprehensive evaluation indicator $Q_0$ is:

$Q_0$=interior CO2 concentration×$p_1$+interior NO2 concentration×$p_2$+interior SO2 concentration×$p_3$+interior PM2.5 concentration×$p_4$+interior VOC concentration×$p_5$+interior dust concentration×$p_6$;

a calculation method of the exterior air comprehensive evaluation indicator $Q_1$ is:

$Q_1$=exterior CO2 concentration×$p_1$+exterior NO2 concentration×$p_2$+exterior SO2 concentration×$p_3$+exterior PM2.5 concentration×$p_4$+exterior VOC concentration×$p_5$+exterior dust concentration×$p_6$;

wherein, $P_1$, $P_2$, $P_3$, $P_4$, $P_5$, and $P_6$ are corresponding weights of pollutants.

As a preferred mode, in step 41, the exterior fresh air volume control model is trained by using a BP neural network algorithm, wherein the weight and threshold of the BP neural network are obtained by quantum particle swarm optimization with self-adaptive weights, including:

step A1: using a position vector of each quantum particle individual in quantum particle swarms as the weight and threshold of the BP neural network, and initializing the position vector parameter of the quantum particle swarm individual to a random number of [−1, 1];

wherein the number of the quantum particle swarms ranges [25, 70], the number of particles in a quantum particle swarm ranges [5, 50], the maximum number of iterations ranges [400, 1000], the number of iterations for forming an elite swarm ranges [60, 180], the premature convergence determination threshold ranges [0.01, 0.45], and the worst particle variation ratio among the swarms δ% ranges [2%, 7%];

step A2: setting a fitness function, and determining the position vector and the number of iterations t of an initial optimal quantum particle individual, wherein t=1;

substituting the weight and threshold corresponding to the position vector of the quantum particle individual into the exterior fresh air volume control model based on the BP neural network, determining the type of an identified vector label by using the exterior fresh air volume control model based on the BP neural network determined from the position vector of the quantum particle individual, and using the reciprocal of the mean square error of the outputted vector label and the actual vector label as a second fitness function;

step A3: calculating a swarm fitness variance of each quantum particle swarm, and performing premature convergence determination;

if the swarm fitness variance of the quantum particle swarm is smaller than a premature convergence determination threshold γ, mutating δ% of worst fitness particles and swarm extreme particles in the quantum particle swarm, and using the current best fitness particles as global optimal quantum particle individuals;

step A4: determining whether to form an elite swarm; when the number of iterations is greater than the number of the elite swarm iterations, extracting extreme values of each swarm by means of information sharing between the swarms to form the elite swarm, and turning to step A8, otherwise, turning to step A5;

step A5: updating particle parameters of the each swarm;

step A6: recalculating and comparing the fitness value of each particle; if the fitness value is superior to the current individual extreme value, updating the individual extreme value; comparing the global extreme particles; if the fitness value of a particle is superior to the current swarm extreme value, updating the global extreme particles, assuming t=t+1, and turning to step A3;

step A7: continuing to evolve the elite swarm;

step A8: determining whether the maximum number of iterations is satisfied, and exiting if it is satisfied, otherwise, assuming t=t+1, and turning to step A3 till the global optimal value is found; and outputting the weight and threshold of the BP neural network.

As a preferred mode, in step 51, the interior air purification control model is trained by using a gray neural network, wherein the weight and threshold of the gray neural network are obtained by optimization using a chaotic bat algorithm, including:

step B1: using the position of a bat individual as the weight and threshold of the interior air purification control model based on the gray neural network, initializing bat swarms, and setting parameters of the bat swarms;

wherein the size of a bat swarm ranges [200, 500], the maximum pulse frequency $r_0$ of the bat individual ranges [0.25, 0.5], the maximum pulse sound intensity $A_0$ ranges [0.25, 0.5], the maximum number of iterations ranges [150, 300], the search accuracy ranges [0.001, 0.1], the pulse frequency ranges [0, 1.5], the bat search frequency increase coefficient ranges [0.02, 0.08], the sound intensity attenuation coefficient ranges [0.8, 0.96], the maximum number of iterations ranges [100, 500], and the maximum search accuracy ranges [0.01, 0.1];

step B2: setting a fitness function, and determining an initial optimal position of the bat individual and the number of iterations t (t=1); substituting the weight and threshold corresponding to the position of the bat individual into the interior air purification control model based on the gray neural network, obtaining a detection result by using the interior air purification control model based on the gray neural network model determined from the position of the bat individual, and constructing a first fitness function f1(x) (f1(x)=1/(E+1)) with the difference E between the detection result and the actual situation;

calculating the fitness of the position of each bat individual by using the first fitness function, and using the position of the bat individual corresponding to the maximum fitness as the initial optimal position of the bat individual;

step B3: updating the speed and position of the bat individual by using a set pulse frequency;

step B4: if Rand1>$r_i$, randomly disturbing the bat at the optimal individual position to generate a disturbance position of the bat individual;

wherein, Rand1 is a random number uniformly distributed on [0, 1], and $r_i$ is a pulse frequency of the i-th bat;

step B5: if Rand2>$A_i$, and the fitness of the disturbed position of the bat individual is superior to the fitness of the position of the bat individual before disturbance, moving the bat individual to the disturbance position, or else keeping the bat individual at the original position;

wherein, Rand2 is a random number uniformly distributed on [0, 1], and $A_i$ is the sound intensity of the i-th bat;

step B6: if the condition of step B5 is satisfied, updating the pulse frequency and pulse sound intensity of the bat individual by using the bat search frequency increase coefficient and the sound intensity attenuation coefficient, and skipping to step B4, or else skipping to step B7;

step B7: calculating the fitness of the position of each bat individual in the current bat swarm, and performing chaotic optimization of position and speed on top m % bat individuals in descending order to obtain updated top m % bat individuals, wherein m ranges [5, 20]; and step B8: determining whether the maximum number of iterations or the maximum search accuracy is reached; if it is reached, selecting a global optimal bat individual from the updated top m % bat individuals according to the fitness value, and outputting the optimal weight and threshold of the interior air purification control model based on the gray neural network corresponding to the global optimal bat individual; otherwise, assuming t=t+1, and turning to step B3 to continue next iteration.

Based on the same inventive concept, the present invention further provides an interior air quality monitoring and ventilation control system for a train, including:

an interior air quality detection module:, configured to acquire interior air quality detection data;

an exterior air quality detection module:, configured to acquire exterior air quality detection data;

a data transmission module:, configured to transmit the acquired interior air quality detection data and the acquired exterior air quality detection data to a data processing module;

the data processing module, configured for modeling and control, wherein: the modeling process includes:

acquiring an interior air comprehensive evaluation index $Q_0$ by using the interior air quality detection data, and acquiring an exterior air comprehensive evaluation index $Q_1$ by using the exterior air quality detection data;

when $Q_0 \geq Q_1$, training an exterior fresh air volume control model according to the following process:

selecting n1 groups of corresponding interior air quality detection data and corresponding exterior air quality detection data as experimental data;

setting the ventilation volume level of a ventilation system of the train to a G1 level;

performing ventilation experiments on the train under the conditions of n1 groups of experimental data, to obtain a minimum ventilation volume level that can reduce the air quality to a human health value within 5 minutes, as a ventilation volume level label corresponding to each group of experimental data;

training an exterior fresh air volume control model by taking the n1 groups of experimental data as input and taking the ventilation volume level labels corresponding to the n1 groups of experimental data as output to obtain the exterior fresh air volume control model;

when $Q_0 < Q_1$, training an interior air purification control model according to the following process:

selecting n2 groups of corresponding interior air quality detection data and corresponding exterior air quality detection data $Q_0 < Q_1$ as experimental data;

setting the ventilation volume level of the ventilation system of the train to a G1 level, and setting the power level of an air purification device to a G2 level;

performing ventilation experiments on the train under the conditions of n2 groups of experimental data, to obtain a minimum ventilation volume level and a minimum power level of the air purification device that can reduce the air quality to the human health value within 5 minutes, wherein the obtained minimum ventilation volume level is used as a ventilation volume level label corresponding to each group of experimental data, and the obtained minimum power level of the air purification device is used as a power level label of the air purification device corresponding to each group of experimental data; and training an interior air purification control model by taking the n2 groups of experimental data as input and taking the ventilation volume level labels and the power level labels of the air purification device corresponding to the n2 groups of experimental data as output to obtain the interior air purification control model;

the control process includes:

obtaining an interior air quality detection data and an exterior air quality detection data;

acquiring an interior air comprehensive evaluation index $Q_0$ by using the interior air quality detection data, and acquiring the exterior air comprehensive evaluation index $Q_1$ by using the exterior air quality detection data;

if $Q_0 \geq Q_1$, calling the exterior fresh air volume control model to obtain the required ventilation volume level and controlling the ventilation system of the high-speed train with the ventilation volume level;

otherwise, calling the interior air purification control model to obtain the required ventilation volume level and power level of the air purification device, controlling the ventilation system of the train with the ventilation volume level, and controlling the air purification device with the power level of the air purification device; and a ventilation control module, including the ventilation system and the air purification device; wherein the ventilation system is configured to ventilate the train according to the ventilation volume level outputted by the data processing module, and the air purification device is configured to purify the air in the train according to the power level of the air purification device outputted by the data processing module.

As a preferred mode, both the interior air quality detection module and the exterior air quality detection module include one or more of a $CO_2$ concentration sensor, a $NO_2$ concentration sensor, a $SO_2$ concentration sensor, a PM2.5 concentration sensor, a VOC concentration sensor, and a dust concentration sensor.

As a preferred mode, the interior air quality detection module includes several interior air quality detection devices, and an interior air quality detection device is arranged at the head, middle and tail of each compartment, respectively; the exterior air quality detection module includes several exterior air quality detection devices, and an exterior air quality detection device is arranged at an outside air inlet of each ventilation duct of each compartment; and every three compartments share a data processing module.

As a preferred mode, the data transmission module includes a wireless transmission module. By setting the several air quality detection modules on the train for acquiring interior and exterior air quality data, processing and analyzing the acquired data, and performing reasonable ventilation control based on the interior and exterior air quality data under different conditions, the present invention has the following advantages:

(1) The air quality in the compartments of the high-speed train is monitored timely and effectively, which ensures the health and comfort of the environment in the compartments of the train and improves the passenger experience.

(2) The interior and exterior integrated monitoring and multi-point monitoring arrangement avoids detection are applied to avoid errors caused by uneven air distribution inside and outside the train, and ensures the accuracy of the acquired results.

(3) Different ventilation control strategies are selected according to different interior and exterior air quality data to avoid interior secondary pollution caused by serious exterior air pollution, and to ensure the stability of the interior air quality.

(4) The control strategies are divided into different levels, and the most reasonable ventilation control level is selected according to different air quality conditions, which maximizes energy conservation while ensuring the ventilation effect and achieves environmental protection.

(5) The ventilation control levels under different air quality conditions are selected by using the neural network, which ensures the effectiveness of selection of the ventilation strategies.

In which: 1 interior air quality detection module, 101 interior air quality detection device, 2 exterior air quality detection module, 201 exterior air quality detection device, 3 data transmission module, 301 wireless transmission module, 4 data processing module, 401 central computer, 5 ventilation control module, 501 ventilation system, 502 air purification device.

DETAILED DESCRIPTION OF EMBODIMENTS

The present invention can monitor the air pollutant concentration inside a train compartment and the air pollutant concentration outside a high-speed train in real time, and select a reasonable ventilation control strategy according to the measured air pollutant concentration data to ensure the air quality inside the compartment of the high-speed train in a healthy state. The selected ventilation strategy is obtained by training a neural network, the input of the model is a variety of measured data, and the output is a ventilation strategy number.

Figure 1:
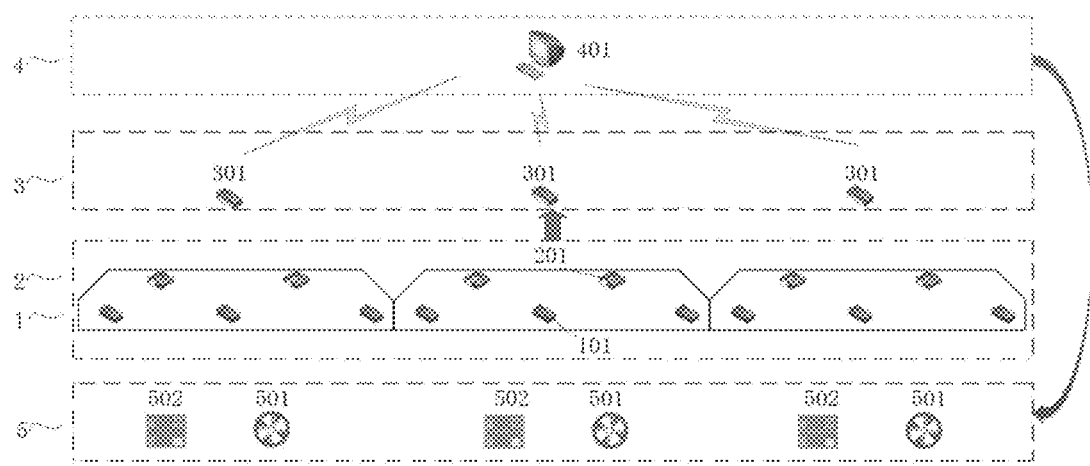
FIG. 1 is a principle diagram of an embodiment of a system according to the present invention.

As shown in FIG. 1, an interior air quality monitoring and ventilation control system for an entire high-speed train includes an interior air quality detection module 1, an exterior air quality detection module 2, a data transmission module 3, a data processing module 4, and a ventilation control module 5. Details of respective modules are as follows:

Interior air quality detection module 1: this module is composed of an interior air quality detection device 101 arranged inside each compartment. Each interior air quality detection device 101 includes a $CO_2$ concentration sensor, a $NO_2$ concentration sensor, a $SO_2$ concentration sensor, a PM2.5 concentration sensor, a VOC sensor, and a dust sensor. An interior air quality detection device 101 is arranged at the head, middle and tail of each compartment, respectively. The data acquired by the interior air quality detection module 1 is transmitted to the data processing module 4 by the data transmission module 3.

Exterior air quality detection module 2: this module is arranged at an outside air inlet of a ventilation duct of each compartment, and each ventilation duct corresponds to an exterior air quality detection device 201. Similar to the interior air quality detection device 101, each exterior air quality detection device 201 includes a $CO_2$ concentration sensor, a $NO_2$ concentration sensor, a $SO_2$ concentration sensor, a PM2.5 concentration sensor, a VOC sensor, and a dust sensor. The data acquired by the exterior air quality detection module 2 is transmitted to the data processing module 4 by the data transmission module 3.

Data transmission module 3: the data transmission module 3 includes a wireless transmission module 301, and each compartment is equipped with a wireless transmission module 301 to connect the interior air quality detection module 1, the exterior air quality detection module 2 and the data processing module 4 to store the acquired data and transmit data between devices. Considering the length of the train, the data can be transmitted by means of a 4G network, which is economical and simple.

Data processing module 4: a central computer 401 is arranged in every three compartments, which is defined as an air quality monitoring area and constitutes the data processing module 4. The central computer 401 is configured to receive interior air acquisition data and exterior air acquisition data acquired from the three compartments within the monitoring range, perform data preprocessing and model training respectively, and output the model training results in time.

Ventilation control module 5: this module is composed of a ventilation system 501 and an air purification device 502 arranged in the ventilation duct of the train. According to the different results outputted by the data processing module 4, a corresponding ventilation control strategy is executed to realize energy conservation and environmental protection of the ventilation system 501 while ensuring qualified air quality in the train.

Figure 2:
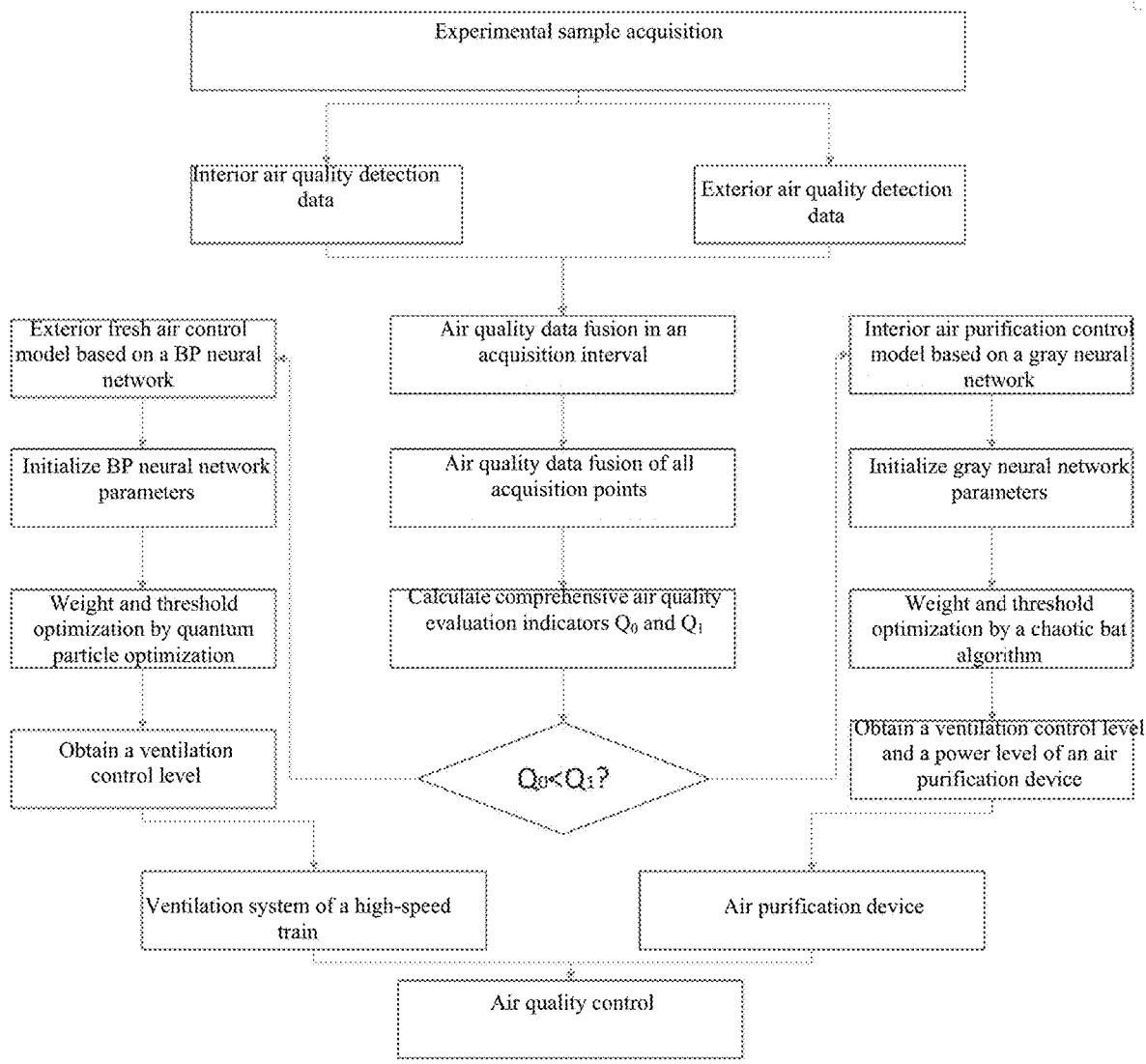
FIG. 2 is a flowchart of an embodiment of a method according to the present invention.

As shown in FIG. 2, an interior air quality monitoring and ventilation control method for an entire high-speed train includes two processes: an off-line training process and an on-line ventilation control process.

Off-Line Training Process:

The method of the present invention first acquires air pollutant concentration information inside and outside the train, and then sends the acquired data to the central computer 401 in the corresponding detection area for data preprocessing and model training. The training model includes two types of neural network models; when various indicators of the interior air pollutant concentration are smaller than the exterior air pollutant concentration indicators, an exterior fresh air volume control model based on a BP neural network is trained, and different levels of ventilation quantities are outputted according to different degrees of interior air pollutant concentration data; and when various indicators of the interior air pollutant concentration are greater than the exterior air pollutant concentration indicators, an interior air purification control model based on a gray neural network is trained. Different levels of ventilation quantities and the power of the air purification device are controlled according to different degrees of interior air pollutant concentration. The entire off-line process is detailed as follows:

1. Interior and Exterior Air Quality Data Acquisition

Different pollutant concentration data is acquired by using the interior air quality detection device 101 and the exterior air quality detection device 201, wherein the acquired interior air quality detection data is expressed as $[I_{CO2}, I_{NO2}, I_{SO2}, I_{pm2.5}, I_{voc}, I_{dust}]$, and the exterior air quality detection data is expressed as $[O_{CO2}, O_{NO2}, O_{SO2}, O_{pm2.5}, O_{voc}, O_{dust}]$. In order to distinguish the data acquired by the air quality detection devices at different positions in different compartments, the formats of interior and exterior air quality data finally transmitted by the wireless transmission module are $[I_{CO2}, I_{NO2}, I_{SO2}, I_{pm2.5}, I_{voc}, I_{dust}, n, m, 0]$ and $[O_{CO2}, O_{NO2}, O_{SO2}, O_{pm2.5}, O_{voc}, O_{dust}, n, m, 1]$, wherein n represents the number of a compartment; m represents the number of an air quality detection device, m=1, 2, 3 for the interior air quality data, and m is determined by the number of contact openings between the ventilation device in each compartment and the outside air for the exterior quality data; 0/1 is a data type identification code, 0 represents that the group of data is interior air quality detection data, and 1 represents that the group of data is exterior air quality detection data.

2. Data Preprocessing

The data of the interior air quality detection device 101 and the exterior air quality detection device 201 are transmitted to the central computer 401 of the data processing module 4 via the wireless transmission module 301 for preprocessing the acquired data. The entire data preprocessing steps are as follows:

(1) Acquiring interior and exterior air quality acquisition data of a target detection compartment at three time points $$t - \frac{N}{2}, t \text{ and } t + \frac{N}{2},$$

and the acquired data at the three time points is averaged to obtain interior air quality detection data $[I_{CO2}, I_{NO2}, I_{SO2}, I_{pm2.5}, I_{voc}, I_{dust}, n, m, 0]$ and exterior air quality detection data $[O_{CO2}, O_{NO2}, O_{SO2}, O_{pm2.5}, O_{voc}, I_{dust}, n, m, 1]$ of each detection point within a time interval of N.

(2) Average processing on the acquired data of all the interior air quality detection points and the acquired data of all the exterior air quality detection points based on the data acquired in step (1) according to the 0/1 identification code and m value of each group of data, and normalize the concentration data of six pollutants, to finally obtain total interior air quality detection data $[I_{CO2total}, I_{NO2total}, I_{SO2total}, I_{pm2.5total}, I_{voctotal}, I_{dusttotal}, n, 0]$ and total exterior air quality detection data $[O_{CO2total}, O_{NO2total}, O_{SO2total}, O_{pm2.5total}, O_{voctotal}, O_{dusttotal}, n, 1]$ of the target detection compartment.

(3) Calculate air quality comprehensive evaluation index, and a calculation method of the air quality comprehensive evaluation index is defined as:

$Q$=CO2 concentration×$p_1$+NO2 concentration×$p_2$+ SO2 concentration×$p_3$+PM2.5 concentration× $p_4$+VOC concentration×$p_5$+dust concentration× $p_6$ Wherein p represents weights of concentration of different pollutants, and $P_1$=0.1, $p_2$=0.1, $p_3$=0.1, $p_4$=0.3, $p_5$=0.2, $p_6$=0.2. Then, the final interior and exterior air quality detection data obtained in step (2) is substituted into the above equation for calculation, to obtain an interior air comprehensive evaluation index $Q_0$ and an exterior air comprehensive evaluation index $Q_1$.

3. Ventilation Control Strategy Model Training (1) An exterior fresh air volume control model is trained, and when $Q_0 \geq Q_1$, the model is used to control the exterior fresh air volume of the ventilation control system.

Interior and exterior air quality data is measured under different outdoor experimental conditions, 1000 groups of interior and exterior air quality data are selected, the ventilation volume levels of the ventilation system 501 of the train are set to four levels 0, 1, 2 and 3, and ventilation experiments are performed on the train under the conditions of 1000 groups of experimental data, to obtain a minimum ventilation volume level that can reduce the air quality to a human health value within 5 min as a label corresponding to each group of experimental data.

The exterior fresh air volume control model is trained by using a BP neural network. The model training input is the interior and exterior air quality detection $[I_{CO2total}, I_{NO2total}, I_{SO2total}, I_{pm2.5total}, I_{voctotal}, I_{dusttotal}, O_{CO2}, O_{NO2}, O_{SO2}, O_{pm2.5}, O_{voc}, O_{dust}]$, and the output is the ventilation volume level label 0, 1, 2, 3 obtained under the ventilation experiment conditions, thus obtaining the exterior fresh air volume control model based on the BP neural network.

The input layer of the BP neural network includes 12 nodes, the output layer includes 1 node, the maximum number of iterations in the training process is set to 500, and the training learning rate is 0.2.

The weight and threshold of the BP neural network in the exterior fresh air volume control model based on the BP neural network are obtained by quantum particle swarm optimization with adaptive weights. The process is as follows:

Step A1: using a position vector of each quantum particle individual in quantum particle swarms as the weight and threshold of the BP neural network, the position vector parameter of the quantum particle swarm individual is initialized to a random number of [−1, 1];

The number of the quantum particle swarms ranges [25, 70], the number of particles in a quantum particle swarm ranges [5, 50], the maximum number of iterations ranges [400, 1000], the number of iterations for forming an elite swarm ranges [60, 180], the premature convergence determination threshold ranges [0.01, 0.45], and the worst particle variation ratio among the swarms δ% ranges [2%, 7%];

Step A2: a fitness function is set, and an initial optimal position vector of the quantum particle individual and the number of iterations t (t=1) are determined;

The weight and threshold corresponding to the position vector of the quantum particle individual are substituted into the exterior fresh air volume control model based on the BP neural network, the type of an identified vector label is determined by using the exterior fresh air volume control model based on the BP neural network determined from the position vector of the quantum particle individual, and the reciprocal of the mean square error of the outputted vector label and the actual vector label is used as a second fitness function;

Step A3: a swarm fitness variance of each quantum particle swarm is calculated, and premature convergence determination is performed;

If the swarm fitness variance of the quantum particle swarm is smaller than a premature convergence determination threshold γ, δ% of worst fitness particles and swarm extreme particles in the quantum particle swarm are mutated, and the best fitness current particles are used as global optimal quantum particle individuals.

Step A4: whether to form an elite swarm is determined;

When the number of iterations is greater than the number of iterations of the elite swarm, extreme values of each swarm are extracted by means of information sharing between the swarms to form the elite swarm, and turning to step A8, otherwise, turning to step A5;

Step A5: particle parameters of each swarm are updated;

Step A6: the fitness value of each particle is recalculated and compared; if the fitness value is superior to the current individual extreme value, the individual extreme value is updated; the global extreme value particles are compared; if the fitness value of a particle is superior to the current swarm extreme value, the global extreme value particles are updated, $t=t+1$ is assumed, and turning to step A3;

Step A7: the elite swarm continues to evolve;

Step A8: to determine whether the maximum number of iterations is satisfied, and if it is satisfied, the process exits, otherwise, assuming $t=t+1$ assumed and turning to step A3 till the global optimal value is found; and outputting the weight and threshold of the BP neural network.

(2) An interior air purification control model is trained, and when $Q_0<Q_1$, the model is used to control the inlet air quantity of the ventilation system 501 and the power of the air purification device 502.

Interior and exterior air quality data is measured under different outdoor experimental conditions, 1000 groups of interior and exterior air quality detection data are selected, the ventilation volume levels of the ventilation system 501 of the high-speed train are set to four levels 0, 1, 2 and 3, and the power values of the air purification device 502 are set to four levels 0, 1, 2, and 3. Then, ventilation experiments are performed on the train under the 1000 groups of experimental data, to obtain a minimum ventilation volume level and a minimum power level of the air purification device 502 that can reduce the air quality to the human health value within 5 min, as a label corresponding to each group of experimental data.

The interior air purification control model is trained by using a gray neural network, the model training input is the interior and exterior air quality detection data: $[I_{CO2total}, I_{NO2total}, I_{SO2total}, I_{pm2.5total}, I_{voctotal}, I_{dusttotal}, O_{CO2}, O_{NO2}, I_{SO2}, O_{pm2.5}, O_{voc}, O_{dust}]$, and the output is the ventilation volume level label and the level label [0/1/2/3, 0/1/2/3] of the air purification device 502 obtained under the ventilation experiment conditions, thus obtaining the interior air purification control model based on the gray neural network.

The number of nodes in the input layer of the interior air purification control model based on the gray neural network is 12, the number of nodes in the hidden layer is 6, and the number of nodes in the output layer is 2; the maximum number of iterations in the training process is set to 500, the training learning rate is 0.1, and the threshold is 0.05.

The weight and threshold of the interior air purification control model based on the gray neural network are obtained by optimization using a chaotic bat algorithm. The process is as follows:

Step B1: using the position of a bat individual as the weight and threshold of a posture anomaly detection model based on the gray neural network, initializing bat swarms, and setting parameters of the bat swarms;

The size of a bat swarm ranges [200, 500], the maximum pulse frequency $r_0$ of the bat individual ranges [0.25, 0.5], the maximum pulse sound intensity $A_0$ ranges [0.25, 0.5], the maximum number of iterations ranges [150, 300], the search accuracy ranges [0.001, 0.1], the pulse frequency ranges [0, 1.5], the bat search frequency increase coefficient ranges [0.02, 0.08], the sound intensity attenuation coefficient ranges [0.8, 0.96], the maximum number of iterations ranges [100, 500], and the maximum search accuracy ranges [0.01, 0.1];

Step B2: setting a fitness function is set, and determining an initial optimal position of the bat individual and the number of iterations t (t=1)

The weight and threshold corresponding to the position of the bat individual are substituted into the interior air purification control model based on the gray neural network, a detection result is obtained by using the interior air purification control model based on the gray neural network model determined from the position of the bat individual, and the difference E between the detection result and the actual situation is used to build a first fitness function $f1(x)$, $f1(x)=1/(E+1)$; The fitness of the position of each bat individual is calculated by using the first fitness function, and the position of the bat individual corresponding to the maximum fitness is used as the initial optimal position of the bat individual;

Step B3: the speed and position of the bat individual are updated by using a set pulse frequency;

Step B4: if Rand1>$r_i$, the bat at the optimal individual position is randomly disturbed to generate a disturbance position of the bat individual;

Wherein, Rand1 is a random number uniformly distributed on [0, 1], and $r_i$ is a pulse frequency of the i-th bat;

Step B5: if Rand2>$A_i$, and the fitness of the disturbance position of the bat individual is superior to the fitness of the position of the bat individual before disturbance, the bat individual is moved to the disturbance position, or else kept at the original position;

Wherein, Rand2 is a random number uniformly distributed on [0, 1], and $A_i$ is the sound intensity of the i-th bat;

Step B6: if the condition of step B5 is satisfied, the pulse frequency and pulse sound intensity of the bat individual are updated by using the bat search frequency increase coefficient and the sound intensity attenuation coefficient, and the process skips to step B4, or else skips to step B7;

Step B7: the fitness of the position of each bat individual in the current bat swarm is calculated, and chaotic optimization of position and speed is performed on top m % bat individuals in descending order to obtain updated top m % bat individuals, wherein m ranges [5, 20];

Step B8: determining whether the maximum number of iterations or the maximum search accuracy is reached; if it is reached, a global optimal bat individual is selected from the updated top m % bat individuals according to the fitness value, and the optimal weight and threshold of the interior air purification control model based on the gray neural network corresponding to the global optimal bat individual are output; otherwise, $t=t+1$ is assumed, and the process turns to step B3 to continue next iteration.

On-Line Ventilation Control Process:

(1) For a certain detection compartment, interior and exterior air quality data is acquired through the interior and exterior air quality detection modules, the data is transmitted to the data processing module 4 through the wireless transmission module 301 for preprocessing, and an interior air comprehensive evaluation index $Q_0$ and an exterior air comprehensive evaluation index $Q_1$ are obtained.

(2) When $Q_0 \geq Q_1$, the interior and exterior air quality data $[I_{CO2total}, I_{NO2total}, I_{SO2total}, I_{pm2.5total}, I_{voctotal}, I_{dusttotal}, O_{CO2total}, O_{NO2total}, O_{SO2total}, O_{pm2.5total}, O_{voctotal}, O_{dusttotal}]$ obtained in the data preprocessing phase is input to the exterior fresh air volume control model based on the BP neural network to obtain an appropriate ventilation volume level 0/1/2/3, and the ventilation system 501 of the train is controlled according to different outputted labels.

(3) When $Q_0 < Q_1$, the interior and exterior air quality data $[I_{CO2total}, I_{NO2total}, I_{SO2total}, I_{pm2.5total}, I_{voctotal}, I_{dusttotal}, O_{CO2total}, O_{NO2total}, O_{SO2total}, O_{pm2.5total}, O_{voctotal}, O_{dusttotal}]$ obtained in the data preprocessing phase is input to the interior air purification control model based on the gray neural network to obtain an appropriate ventilation volume level and a power level [0/1/2/3, 0/1/2/3] of the air purification device 502, and the ventilation system 501 and the air purification device 502 of the train are controlled according to different outputted labels.

The embodiments of the present invention are described above with reference to the drawings, but the present invention is not limited to the specific embodiments. The specific embodiments described above are merely illustrative but not limited. Many forms may also be made by those of ordinary skill in the art under the enlightenment of the present invention without departing from the purpose of the present invention and the scope of the claims, and these forms fall into the scope of the present invention.

The invention claimed is:

1. A modeling method for a train interior air quality monitoring and ventilation control model, comprising the following steps:
   A) acquiring a plurality of groups of a first interior air quality detection data and a first exterior air quality detection data;
   B) acquiring an interior air comprehensive evaluation index (Q0) by using the first interior air quality detection data, and acquiring an exterior air comprehensive evaluation index (Q1) by using the first exterior air quality detection data;
   C) determining the magnitude relationship between the interior air comprehensive evaluation index Q0 and the exterior air comprehensive evaluation index Q1;
   D) when the exterior air comprehensive evaluation index is less than the interior air comprehensive evaluation index, training an exterior fresh air volume control model according to the following method:
      selecting first groups of corresponding first interior air quality detection data and corresponding first exterior air quality detection data as experimental data;
      setting the ventilation volume level of a ventilation system of the high-speed train to a first level;
      performing ventilation experiments on the train under the conditions of the first groups of experimental data, to obtain a minimum ventilation volume level that can reduce the air quality to a human health value within 5 minutes, as a ventilation volume level label corresponding to each group of experimental data; and
      training an exterior fresh air volume control model by taking the first groups of experimental data as input and taking the ventilation volume level labels corresponding to the first groups of experimental data as output to obtain the exterior fresh air volume control model;
   E) when the exterior air comprehensive evaluation index is not less than the interior air comprehensive evaluation index, training an interior air purification control model according to the following method:
      selecting second groups of the corresponding first interior air quality detection data and the corresponding first exterior air quality detection data as experimental data;
      setting the ventilation volume level of the ventilation system of the high-speed train to the first level, and setting the power level of an air purification device to a second level;
      performing ventilation experiments on the train under the conditions of the second groups of experimental data, to obtain a minimum ventilation volume level and a minimum power level of the air purification device that can reduce the interior air quality to the human health value within 5 minutes, wherein the obtained minimum ventilation volume level is used as a ventilation volume level label corresponding to each group of experimental data, and the obtained minimum power level of the air purification device is used as a power level label of the air purification device corresponding to each group of experimental data; and
      training an interior air purification control model by taking the second groups of experimental data as input and taking the ventilation volume level labels and the power level labels of the air purification device corresponding to the second groups of experimental data as output to obtain the interior air purification control model; and
   F) using the trained exterior fresh air volume control model and the trained interior air purification control model as the train interior air quality monitoring and ventilation control model.

2. The modeling method for a train interior air quality monitoring and ventilation control model according to claim 1, wherein the first interior air quality detection data and the first exterior air quality detection data both comprise one or more of $CO_2$ concentration, $NO_2$ concentration, $SO_2$ concentration, PM2.5 concentration, VOC concentration, and dust concentration.

3. The modeling method for a train interior air quality monitoring and ventilation control model according to claim 1, wherein at least one of the first interior air quality detection data and the first exterior air quality detection data are obtained by a multi-point monitoring mode.

4. The modeling method for a train interior air quality monitoring and ventilation control model according to claim 1, wherein a calculation method of the interior air comprehensive evaluation indicator Q0 is:

$Q0$=interior $CO_2$ concentration$\times p_1$+interior $NO_2$ concentration$\times p_2$+interior $SO_2$ concentration$\times p_3$+interior $PM2.5$ concentration$\times p_4$+interior $VOC$ concentration$\times p_5$+interior dust concentration$\times p_6$; and a calculation method of the exterior air comprehensive evaluation indicator $Q_1$ is:

$Q1$=exterior $CO_2$ concentration$\times p_1$+exterior $NO_2$ concentration$\times p_2$+exterior $SO_2$ concentration$\times$ $p_3$+exterior $PM2.5$ concentration×$p_4$+exterior $VOC$ concentration×$p_5$+exterior dust concentration×$p_6$;

wherein, $P_1$, $P_2$, $P_3$, $P_4$, $P_5$, and $P_6$ are corresponding weights of pollutants.

5. The modeling method for a train interior air quality monitoring and ventilation control model according to claim 1, wherein in step D), the exterior fresh air volume control model is trained by using a BP neural network algorithm, wherein the weight and threshold of the BP neural network are obtained by quantum particle swarm optimization with self-adaptive weights, comprising:
   D1) using a position vector of each quantum particle individual in quantum particle swarms as the weight and threshold of the BP neural network, and initializing the position vector parameter of the quantum particle swarm individual to a random number of [−1, 1];
      wherein the number of the quantum particle swarms ranges [25, 70], the number of particles in a quantum particle swarm ranges [5, 50], the maximum number of iterations ranges [400, 1000], the number of iterations for forming an elite swarm ranges [60, 180], the premature convergence determination threshold ranges [0.01, 0.45], and the worst particle variation ratio among the swarms δ% ranges [2%, 7%];
   D2) setting a fitness function, and determining the position vector and the number of iterations t of an initial optimal quantum particle individual, wherein t=1; substituting the weight and threshold corresponding to the position vector of the quantum particle individual into the exterior fresh air volume control model based on the BP neural network, determining the type of an identified vector label by using the exterior fresh air volume control model based on the BP neural network determined from the position vector of the quantum particle individual, and using the reciprocal of the mean square error of the outputted vector label and the actual vector label as a second fitness function;
   D3) calculating a swarm fitness variance of each quantum particle swarm, and performing premature convergence determination;
      if the swarm fitness variance of the quantum particle swarm is smaller than a premature convergence determination threshold γ, mutating δ% of worst fitness particles and swarm extreme particles in the quantum particle swarm, and using the current best fitness particles as global optimal quantum particle individuals;
   D4) determining whether to form an elite swarm;
      when the number of iterations is greater than the number of iterations for forming the elite swarm, extracting extreme values of each swarm by means of information sharing between the swarms to form the elite swarm, and turning to step D8), otherwise, turning to step D5);
   D5) updating particle parameters of each swarm;
   D6) recalculating and comparing the fitness value of each particle; if the fitness value is superior to the current individual extreme value, updating the individual extreme value; comparing the global extreme particles; if the fitness value of a particle is superior to the current swarm extreme value, updating the global extreme particles, assuming t=t+1, and turning to step D3);
   D7) continuing to evolve the elite swarm; and
   D8) determining whether the maximum number of iterations is satisfied, and exiting if it is satisfied, otherwise, assuming t=t+1, and turning to step D3) till the global optimal value is found; and outputting the weight and threshold of the BP neural network.

6. The modeling method for a train interior air quality monitoring and ventilation control model according to claim 1, wherein in step E), the interior air purification control model is trained by using a gray neural network, wherein the weight and threshold of the gray neural network are obtained by optimization using a chaotic bat algorithm, comprising:
   E1) using the position of a bat individual as the weight and threshold of the interior air purification control model based on the gray neural network, initializing bat swarms, and setting parameters of the bat swarms;
      wherein the size of a bat swarm ranges [200, 500], the maximum pulse frequency r0 of the bat individual ranges [0.25, 0.5], the maximum pulse sound intensity A0 ranges [0.25, 0.5], the maximum number of iterations ranges [150, 300], the search accuracy ranges [0.001, 0.1], the pulse frequency ranges [0, 1.5], the bat search frequency increase coefficient ranges [0.02, 0.08], the sound intensity attenuation coefficient ranges [0.8, 0.96], the maximum number of iterations ranges [100, 500], and the maximum search accuracy ranges [0.01, 0.1];
   E2) setting a fitness function, and determining an initial optimal position of the bat individual and the number of iterations t, t=1; substituting the weight and threshold corresponding to the position of the bat individual into the interior air purification control model based on the gray neural network, obtaining a detection result by using the interior air purification control model based on the gray neural network model determined from the position of the bat individual, and building a first fitness function f1 (E) with the difference E between the detection result and the actual situation, wherein f1(E) =1/(E+1);
      calculating the fitness of the position of each bat individual by using the first fitness function, and using the position of the bat individual corresponding to the maximum fitness as the initial optimal position of the bat individual;
   E3) updating the speed and position of the bat individual by using a set pulse frequency;
   E4) if Rand1>$r_i$, randomly disturbing the bat at the optimal individual position to generate a disturbance position of the bat individual;
      wherein, Rand1 is a random number uniformly distributed on [0, 1], and $r_i$ is a pulse frequency of the i-th bat;
   E5): if Rand2>$A_i$, and the fitness of the disturbed position of the bat individual is superior to the fitness of the position of the bat individual before disturbance, moving the bat individual to the disturbance position, or else keeping the bat individual at the original position;
      wherein, Rand2 is a random number uniformly distributed on [0, 1], and $A_i$ is the sound intensity of the i-th bat;
   E6) if the condition of step E5) is satisfied, updating the pulse frequency and pulse sound intensity of the bat individual by using the bat search frequency increase coefficient and the sound intensity attenuation coefficient, and returning to step E4), or else continuing to step E7);
   E7) calculating the fitness of the position of each bat individual in the current bat swarm, and performing chaotic optimization of position and speed on top m % bat individuals in descending order to obtain updated top m % bat individuals, wherein m ranges [5, 20]; and E8) determining whether the maximum number of iterations or the maximum search accuracy is reached; if it is reached, selecting a global optimal bat individual from the updated top m % bat individuals according to the fitness value, and outputting the optimal weight and threshold of the interior air purification control model based on the gray neural network corresponding to the global optimal bat individual; otherwise, assuming t=t+1, and turning to step E3) to continue next iteration.

7. A train interior air quality monitoring and ventilation control model obtained by using the modeling method for a train interior air quality monitoring and ventilation control model according to claim 1.

8. A method for train interior air quality monitoring and ventilation control, comprising:
   G) detecting a second interior air quality detection data and a second exterior air quality detection data;
   H) acquiring an interior air comprehensive evaluation index Q0 by using the second interior air quality detection data in step G) and acquiring an exterior air comprehensive evaluation index Q1 by using the second exterior air quality detection data in step G); and
   I) determining the magnitude relationship between the interior air comprehensive evaluation index Q0 and the exterior air comprehensive evaluation index Q1 obtained in H), when the exterior air comprehensive evaluation index is less than the interior air comprehensive evaluation index, calling the train interior air quality monitoring and ventilation control model obtained by using the modeling method for a train interior air quality monitoring and ventilation control model according to claim 1 to obtain the required ventilation volume level and controlling the ventilation system of the high-speed train with the ventilation volume level;
      when the exterior air comprehensive evaluation index is not less than the interior air comprehensive evaluation index, calling the train interior air quality monitoring and ventilation control model obtained by using the modeling method for a train interior air quality monitoring and ventilation control model according to claim 1 to obtain the required ventilation volume level and power level of the air purification device, controlling the ventilation system of the high-speed train with the ventilation volume level, and controlling the air purification device with the power level of the air purification device.

9. The method for train interior air quality monitoring and ventilation control according to claim 8, wherein the second interior air quality detection data and the second exterior air quality detection data both comprise one or more of $CO_2$ concentration, $NO_2$ concentration, $SO_2$ concentration, PM2.5 concentration, VOC concentration, and dust concentration.

10. The method for train interior air quality monitoring and ventilation control according to claim 8, wherein at least one of the second interior air quality detection data and the second exterior air quality detection data are obtained by a multi-point monitoring mode.

11. A modeling system for a train interior air quality monitoring and ventilation control model, comprising:
   an interior air quality detection module, configured to acquire a first interior air quality detection data;
   an exterior air quality detection module, configured to acquire a first exterior air quality detection data;
   a data transmission module, configured to transmit the acquired first interior air quality detection data and the acquired first exterior air quality detection data to a data processing module;
   the data processing module configured for modeling; wherein:
      the modeling process comprises:
         acquiring an interior air comprehensive evaluation index Q0 by using the first interior air quality detection data, and acquiring an exterior air comprehensive evaluation index Q1 by using the first exterior air quality detection data;
         when Q0≥Q1, training an exterior fresh air volume control model according to the following process:
         selecting first groups of the corresponding first interior air quality detection data and the corresponding first exterior air quality detection data as experimental data;
         setting the ventilation volume level of a ventilation system of the train to a first level;
         performing ventilation experiments on the train under the conditions of the first groups of experimental data, to obtain a minimum ventilation volume level that can reduce the air quality to a human health value within 5 minutes, as a ventilation volume level label corresponding to each group of experimental data; and
         training an exterior fresh air volume control model by taking the first groups of experimental data as input and taking the ventilation volume level labels corresponding to the n1 groups of experimental data as output to obtain the exterior fresh air volume control model;
         when Q0<Q1, training an interior air purification control model according to the following process:
         selecting second groups of the corresponding first interior air quality detection data and the corresponding first exterior air quality detection data as experimental data;
         setting the ventilation volume level of the ventilation system of the train to the first level, and setting the power level of an air purification device to a second level;
         performing ventilation experiments on the train under the conditions of the second groups of experimental data, to obtain a minimum ventilation volume level and a minimum power level of the air purification device that can reduce the air quality to the human health value within 5 minutes, wherein the obtained minimum ventilation volume level is used as a ventilation volume level label corresponding to each group of experimental data, and the obtained minimum power level of the air purification device is used as a power level label of the air purification device corresponding to each group of experimental data; and
         training an interior air purification control model by taking the second groups of experimental data as input and taking the ventilation volume level labels and the power level labels of the air purification device corresponding to the second groups of experimental data as output to obtain the interior air purification control model;
      the train interior air quality monitoring and ventilation control model includes the trained exterior fresh air volume control model and the trained interior air purification control model.

12. The modeling system for a train interior air quality monitoring and ventilation control model according to claim 11,
wherein both the interior air quality detection module and the exterior air quality detection module comprise one or more of a $CO_2$ concentration sensor, a $NO_2$ concentration sensor, a $SO_2$ concentration sensor, a PM2.5 concentration sensor, a VOC concentration sensor, and a dust concentration sensor.

13. The modeling system for a train interior air quality monitoring and ventilation control model according to claim 11, wherein
the interior air quality detection module comprises several interior air quality detection devices, and an interior air quality detection device is arranged at a head, a middle and a tail of each compartment, respectively;
the exterior air quality detection module comprises several exterior air quality detection devices, and an exterior air quality detection device is arranged at an outside air inlet of each ventilation duct of each compartment; and
every three compartments share a data processing module.

14. The modeling system for a train interior air quality monitoring and ventilation control model according to claim 11, wherein the data transmission module comprises a wireless transmission module.

15. A train interior air quality monitoring and ventilation control system, comprising the modeling system for a train interior air quality monitoring and ventilation control model according to claim 11, wherein:
the interior air quality detection module is also configured to acquire a first interior air quality detection data;
the exterior air quality detection module is also configured to acquire a first exterior air quality detection data;
the data transmission module is also configured to transmit the acquired first interior air quality detection data and the acquired first exterior air quality detection data to a data processing module;
the data processing module is also configured for control; wherein:
the control process comprises:
obtaining an second interior air quality detection data and an second exterior air quality detection data;
acquiring the interior air comprehensive evaluation index Q0 by using the second interior air quality detection data, and acquiring the exterior air comprehensive evaluation index Q1 by using the second exterior air quality detection data;
if Q0≥Q1, calling the exterior fresh air volume control model to obtain the required ventilation volume level and controlling the ventilation system of the high-speed train with the ventilation volume level;
otherwise, calling the interior air purification control model to obtain the required ventilation volume level and power level of the air purification device, controlling the ventilation system of the high-speed train with the ventilation volume level, and controlling the air purification device with the power level of the air purification device; and
further comprising a ventilation control module, which comprising the ventilation system and the air purification device; wherein the ventilation system is configured to ventilate the train according to the ventilation volume level outputted by the data processing module, and the air purification device is configured to purify the air in the train according to the power level of the air purification device outputted by the data processing module.

* * * * *